United States Patent [19]

Qian

[11] Patent Number: 5,047,028

[45] Date of Patent: Sep. 10, 1991

[54] METHOD FOR INDUCING THROMBOSIS IN BLOOD VESSELS

[76] Inventor: Quinghua Qian, Schittenhelmstrafe 12, 2300 Kiel 1, Fed. Rep. of Germany

[21] Appl. No.: 518,163

[22] Filed: May 3, 1990

[30] Foreign Application Priority Data

May 12, 1989 [DE] Fed. Rep. of Germany ....... 3915636

[51] Int. Cl.$^5$ ............................................. A61B 17/36
[52] U.S. Cl. ...................................... 606/49; 128/786
[58] Field of Search ............................. 606/32, 41, 49; 128/639, 640, 642, 419 D, 419 PG, 784–786

[56] References Cited

U.S. PATENT DOCUMENTS

| | | | |
|---|---|---|---|
| 4,522,205 | 6/1985 | Taylor et al. ............................ | 606/49 |
| 4,574,807 | 3/1986 | Hewson et al. ................ | 128/419 PG |
| 4,717,381 | 1/1988 | Papantonakos ......................... | 128/786 |
| 4,776,349 | 10/1988 | Nashef et al. ......................... | 128/786 |
| 4,960,133 | 10/1990 | Hewson ................................ | 128/642 |
| 4,979,948 | 12/1990 | Geddes et al. ......................... | 606/33 |

FOREIGN PATENT DOCUMENTS 3516830 11/1986 Fed. Rep. of Germany ...... 128/786

*Primary Examiner*—Lee S. Cohen
*Assistant Examiner*—Krista M. Pfaffle
*Attorney, Agent, or Firm*—Herbert W. Larson

[57] ABSTRACT

Method of employing a balloon tube for creating a thrombosis of vessels located directly under the surface of a body cavity which is difficult to reach, through the initiation of an electric current between the balloon which is deflated as introduced into the body cavity and which is inflated by introducing a fluid on the spot and an outside electrode. The fluid which is used to inflate the balloon is electrically conductive and the balloon wall is semi-permeable for the fluid.

13 Claims, 1 Drawing Sheet

METHOD FOR INDUCING THROMBOSIS IN BLOOD VESSELS

BACKGROUND OF THE INVENTION

1. Field of the Invention

This invention relates to methods employing balloon tubes in medical practice. More particularly, the invention concerns a method of using a balloon tube for inducing thrombosis in blood vessels located directly under the surface of a cavity in the body which is difficult to reach.

2. Description of the Prior Art

Balloon tubes are known from T. V. Taylor and J. M. M. Neilson's article "Currents and Clots" —an approach to the problem of acute variceal bleeding". Br. J. Surg. Vol. 68 (1981) 692-696. It is known how to stop bleeding of vessels located directly under the surface of a difficult to reach body cavity, through thrombosis by introducing a deflated balloon tube into the body cavity and then inflating it by applying a fluid at the correct position. The balloon tube from the previous proposal is furnished with electrodes on its outer surface. These electrodes are supplied with a voltage across an electrically conductive wire. An electrode, possibly placed on the patient's back, can serve as an oppositely charged electrode. The electric current which arises through the application of voltage between the two electrodes induces thrombosis and therefore acts to stop the bleeding of the vessels.

Such thrombosis in bleeding vessels is indicated especially for oesophageal varices but could also be involved in bleeding in other body cavities.

The balloon tube which is known from the above-named article has not been able to assert itself in practice, since the resistance between the electrode and the surface of the body cavity is not defined.

SUMMARY OF THE INVENTION

The aim of the invention is to further develop the balloon tube as it is already known, so that it suffices for the demands of practical use.

Through this invention this problem can be solved by the fact that the fluid which serves to inflate the balloon is capable of carrying an electric current and the membrane wall of the balloon is semi-permeable for the fluid.

The wire, which is to be led through the tube, should preferably be made of platinum.

Normal saline solution can be used as the fluid. Other electrically conductive fluids, such as electrode gel, can be used. The fluid can also serve as a conductor of medication.

BRIEF DESCRIPTION OF THE DRAWINGS

The invention is explained by the following description and drawings in which.

DETAILED DESCRIPTION OF THE INVENTION

Figure 1:
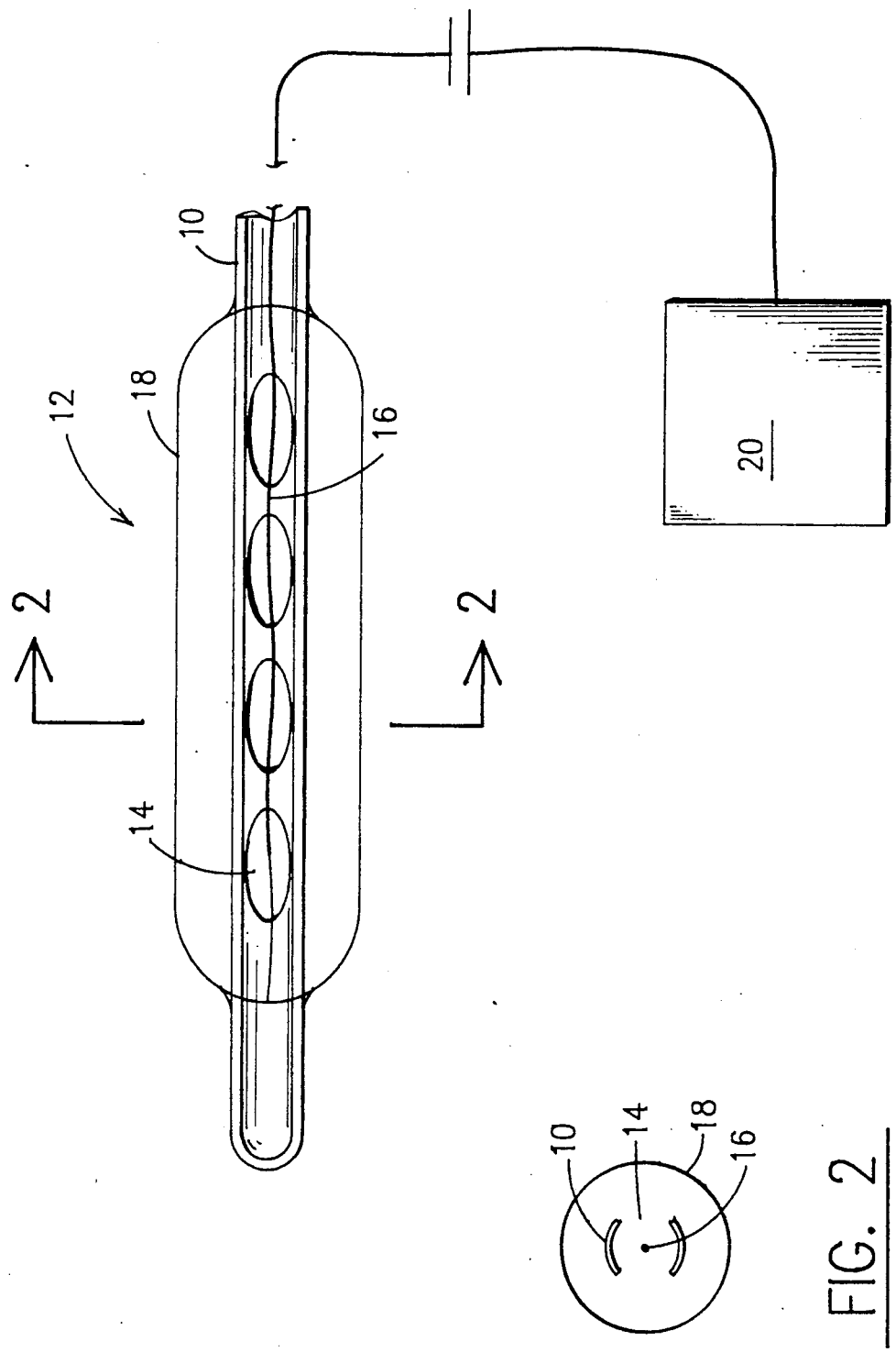
FIG. 1 shows a cross-section through the balloon tube, whereby the upper part of the tube has been cut off
Figure 2:
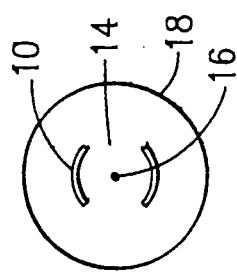
FIG. 2 shows a cross-section along the line II—II from FIG. 1.

Throughout the following detailed description, the same reference numerals refer to the same elements in all figures.

The balloon tube which has been used corresponds in its appearance at first glance to a normal Sengstaken-Tube. It consists of a tube 10 and a balloon 12 located near the end of tube 10. Tube 10 is furnished with openings 14 in the area in which the tube 10 is led through balloon 12. A conductive wire 16 is led through tube 10. Preferably, the conductive wire is made from platinum.

As an example, to stop bleedings of the oesophageal varices, the balloon tube is introduced into the oesophagus, whereby balloon 12 is deflated. When the desired place has been reached, a conductive fluid, for example, normal saline solution, is introduced into the tube 10. The fluid enters balloon 12 through the openings 14 in tube 10 and fills it. The balloon membrane walls 18 are of a semipermeable nature. Therefore, a small amount of the conducting fluid flows through the balloon walls 18. The balloon wall 18 offers no significant electrical resistance.

A counter electrode 20 with a large surface area is applied to the chest area of the patient in the case of thrombosis of oesophageal varices.

By applying a source of voltage between the platinum wire 16 and the counter electrode 20 with opposite charge, a current arises between these two which induces the desired thrombosis through the choice of a suitable voltage difference between them.

The special wire 16 is not absolutely necessary, but rather the conductive fluid found in the tube also can be used as an electric conductor. Tube 10 is not semipermeable and therefore offers considerable electric resistance.

Instead of a normal saline solution, a substance such as electrode gel, for example, also can be used as a conducting fluid.

The balloon tube suggested here can further be used for example for the treatment of post-operative rebleedings after urethra operations or by lower intestinal bleedings or also by nasopharyngeal bleedings.

A further method is to add medicaments to the conducting fluid which induce blood-stanching over an iontophoretic tissue diffusion.

I claim:

1. Method for creating a thrombosis in a blood vessel located directly under the surface of a body cavity which is difficult to reach comprising inserting a deflated balloon containing a cylindrical tube into the body cavity, the tube having openings to the balloon, inflating the balloon by introducing an electrically conductive fluid into the tube, the balloon having an exterior wall semi-permeable to the fluid, contacting a conductive wire to the conductive fluid to provide a connection to an electrode outside the body and initiating an electric current between the balloon and the electrode located outside the body cavity.

2. The method according to claim 1 wherein a wire is inserted through the cylindrical tube and is connected to the electrode located outside the body cavity.

3. The method according to claim 2 wherein the wire inserted is made of platinum.

4. The method according to claim 3 wherein the fluid introduced is normal saline solution.

5. The method according to claim 2 wherein the fluid introduced is normal saline solution.

6. The method according to claim 1 wherein the fluid introduced is normal saline solution.

7. The method according to claim 6, the method further comprising a step of adding a medicament to the fluid.

8. The method according to claim 1, the method further comprising a step of adding a medicament to the fluid.

9. An apparatus for inducing thrombosis in hard to reach blood vessels within a living body comprising
- a cylindrical tube having multiple lateral passageways,
- an electrically conductive fluid located within the tube,
- a balloon having a membrane wall semipermeable to the fluid surrounding a portion of the cylindrical tube containing the passageways,
- a counter electrode adapted to be located outside the body and
- an electrically conductive wire electrically connecting the fluid and the electrode.

10. An apparatus according to claim 9 wherein the fluid is normal saline solution.

11. An apparatus according to claim 9 wherein the wire is made of platinum and the fluid is normal saline solution.

12. An apparatus according to claim 11 wherein a medicament is present in the fluid.

13. An apparatus according to claim 9 wherein a medicament is present in the fluid.

* * * * *